United States Patent [19]

Crump

[11] 4,232,671

[45] Nov. 11, 1980

[54] SAFETY EYEWASH PACKAGE AND CONTAINER THEREFOR

[76] Inventor: Charles L. Crump, 151 Fuller La., Winnetka, Ill. 60093

[21] Appl. No.: 918,364

[22] Filed: Jun. 23, 1978

[51] Int. Cl.[3] ............ A61M 7/00

[52] U.S. Cl. ............ 128/249; 222/107; 401/8; 401/183; 401/265

[58] Field of Search ............ 401/6-8, 401/28, 183, 186, 265, 132; 128/232, 248, 249; 239/327, 328; 222/105, 107, 210, 215

[56] References Cited

U.S. PATENT DOCUMENTS

| | | | |
|---|---|---|---|
| 1,006,945 | 10/1911 | Houston | 128/249 |
| 1,064,641 | 6/1913 | Halstead | 401/28 |
| 1,900,201 | 3/1933 | Sager | 128/249 |
| 2,044,428 | 6/1936 | Gilmer | 401/8 |
| 2,561,071 | 7/1951 | Prisk | 128/272 |
| 2,771,224 | 11/1956 | Boerger | 222/210 |
| 2,790,982 | 5/1957 | Schneider | 401/7 |
| 2,878,967 | 3/1959 | Duke | 222/107 |
| 3,121,511 | 2/1964 | Whitehead | 128/249 X |
| 3,162,339 | 12/1964 | Le Cluyse | 222/105 X |
| 3,231,145 | 1/1966 | Converse | 401/186 |
| 3,276,067 | 10/1966 | Boyle et al. | 401/186 |
| 3,567,074 | 3/1971 | Brown | 222/107 |
| 3,775,014 | 11/1973 | Roseborne | 401/8 |
| 3,806,260 | 4/1974 | Miller | 401/7 |
| 3,818,909 | 6/1974 | Bratton | 128/249 X |
| 3,820,904 | 6/1974 | Lindgren | 401/6 |
| 3,856,142 | 12/1974 | Vessalo | 128/272 X |
| 3,871,554 | 3/1975 | Huck | 222/96 |
| 3,917,119 | 11/1975 | Kahn | 128/249 X |
| 3,930,500 | 1/1976 | Mohrke et al. | 128/249 X |

FOREIGN PATENT DOCUMENTS

| | | | |
|---|---|---|---|
| 102870 | 1/1917 | United Kingdom | 128/249 |
| 435790 | 9/1935 | United Kingdom | 401/8 |

*Primary Examiner*—Steven A. Bratlie

*Attorney, Agent, or Firm*—Claron N. White

[57] ABSTRACT

A safety eyewash has an eyewash liquid in a container that has two flexible plastic sheets that are sealed around the bottom and end margins and are sealed at the top margin after the liquid is placed in the container. One of the sheets has two sets of holes that are covered by a removable strip of liquid-impervious material secured on that sheet. The size of the holes is such that there is no substantial passage of the liquid through the holes after the strip has been removed until the container is subjected to a compressive force that results in streams of liquid passing out of the holes. The spacing between the centers of the sets of holes is an interpupillary distance. A hand strap can be mounted on the other plastic sheet.

6 Claims, 8 Drawing Figures

FIG. 5
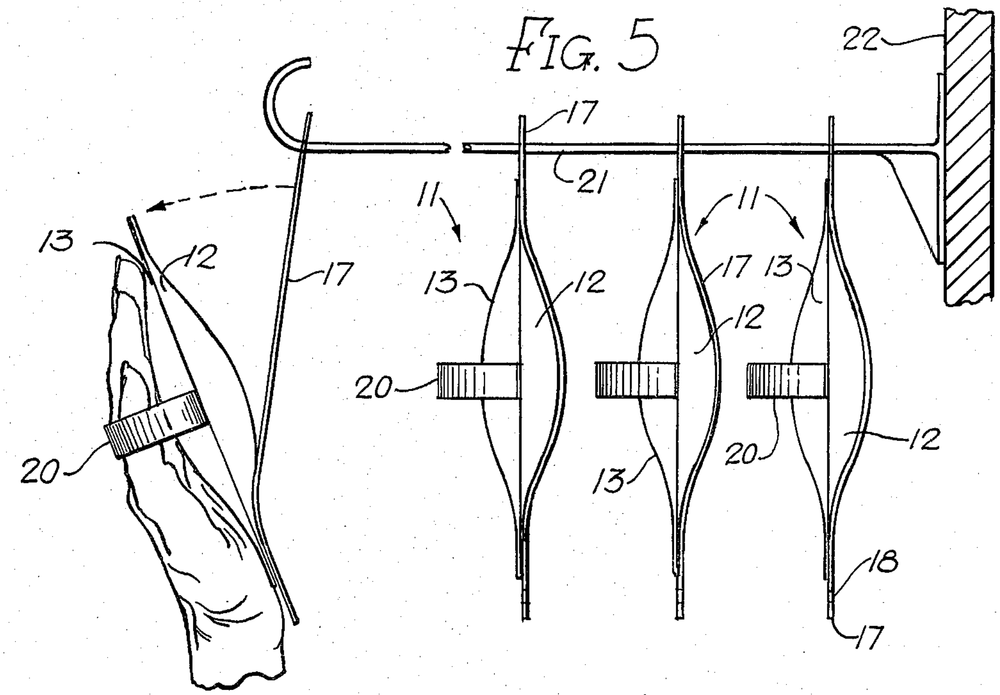
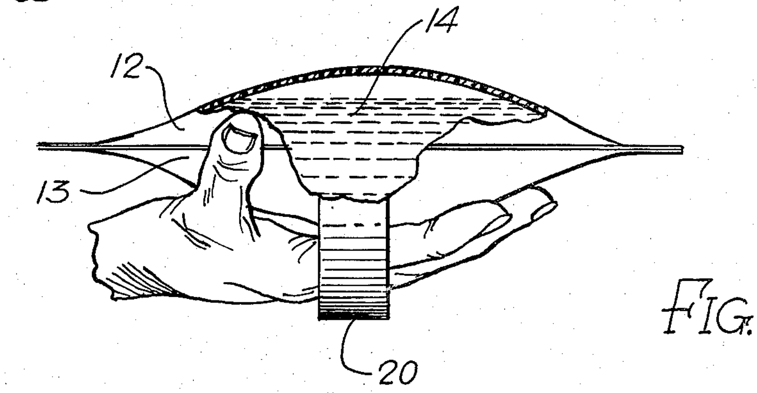
FIG. 6
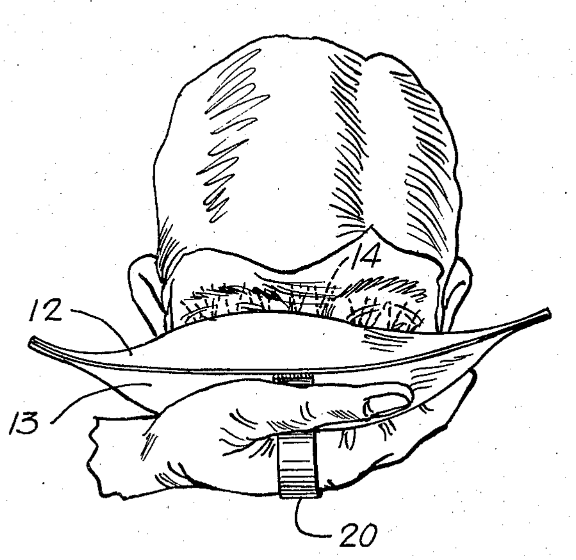
FIG. 7
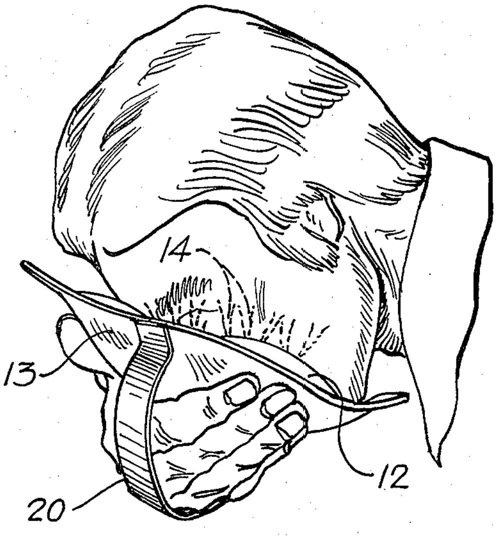
FIG. 8

SAFETY EYEWASH PACKAGE AND CONTAINER THEREFOR

BRIEF SUMMARY OF THE INVENTION

A safety eyewash package comprises a sealed container that contains an eyewash liquid that can be water or a liquid medicament. The container includes a flexible front wall having a set of holes. Except for the holes in the front wall, the container is impervious to the liquid in the container. A removable strip of liquid-impervious material is secured on the front wall and a portion of the strip overlies the set of holes to prevent the loss of liquid through the holes if a compressive force is applied to the package.

The front wall of the container is flexible to conform partially to the upper part of the face of an individual when the package is pressed against that part of the face. The holes of the set are sufficiently small so that there is either no passage or no substantial passage of liquid in the package through the holes after the strip has been removed but the size of the holes is sufficient to pass streams of liquid through the holes whenever the front wall of the container, after removal of the strip, is pressed against the front of the face by a compressive force against the back of the container. The set of holes are located so that they will be at the area of one eye of the person to provide the stream of liquid when the package, with the strip removed, is pressed against the face.

In the preferred construction of the container, its front wall has two spaced sets of holes and the strip of the package covers both sets. The spacing of the two sets is such that each will overlie a different eye of the person to provide streams of liquid from the package to both eyes, after the strip is removed, when the front wall of the package is positioned against the face and the compressive force is applied to the rear of the package.

The container is preferably made of a plastic material, such as polyethylene, that is impervious to the liquid in this preferred construction. The bottom and end margins of two sheets of plastic, illustratively about 6" high and about 8" wide when having the two sets of holes, are sealed to each other. The top margin is sealed after the liquid has been placed in the container. The walls of such container are flexible and have an illustrative thickness of about 0.5 mm. The front sheet has the set or two spaced sets of holes, with each hole illustratively having a diameter of about 0.8 mm. Such hole size, after removal of the strip, produces a stream of liquid through it with sufficient direction and force to provide an eyewash when the package is compressed but the hole does not bleed liquid until the compressive force is applied. By the combination of such hole size with the two spaced sets of holes in the front sheet and with the container holding about one pint of eyewash, the package after removal of the strip and then pressing the package against the face of the individual will provide about two minutes of flooding liquid to the two eyes of the individual.

As seen in the detailed description of the preferred embodiment of construction of package of the invention, a strap is mounted on the outer surface of the real wall of the container for insertion between the strap and the rear wall of fingers of one hand of the individual to lift the package, with the strip removed, and press the package against his face for a washing of his eye or eyes with the liquid in the package. The user can control the flow rate by the pressure applied by the hand.

DESCRIPTION OF THE DRAWINGS

The drawings show a preferred embodiment of the package of the invention with the two sets of holes.

FIG. 5 is a side view of a number of the packages on a horizontal hanger, that is mounted on a wall and that has its free end upwardly hooked, showing a separation of the package from its strip when the package is moved to the free end of the hanger and the hand in the strap provide a peeling force.

FIG. 6 shows the package, after the strip is removed and with a hand still supporting it and fingers of the hand extending between the rear strap and the back wall of the package.

FIGS. 7 and 8 are schematic front and side views of the package, with the rear strip removed, pressed by the hand against the face of the individual and showing liquid streaming from the container toward the eyes of the individual.

DETAILED DESCRIPTION

Figure 1:
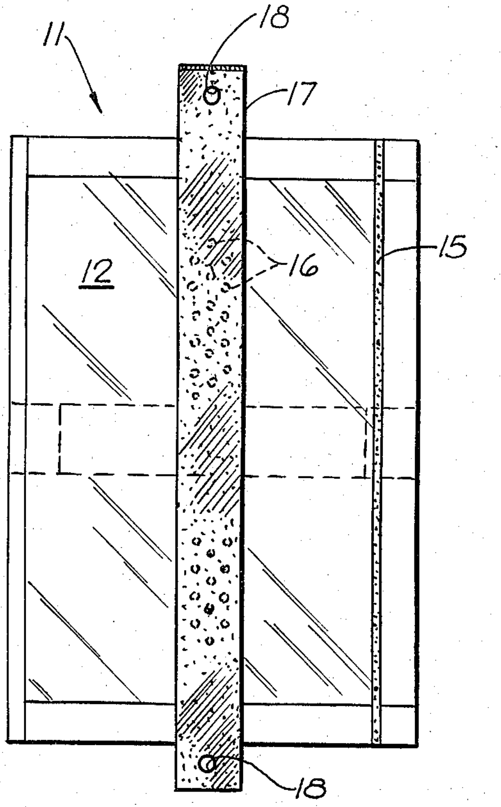
FIG. 1 is a front view of the package.
Figure 2:
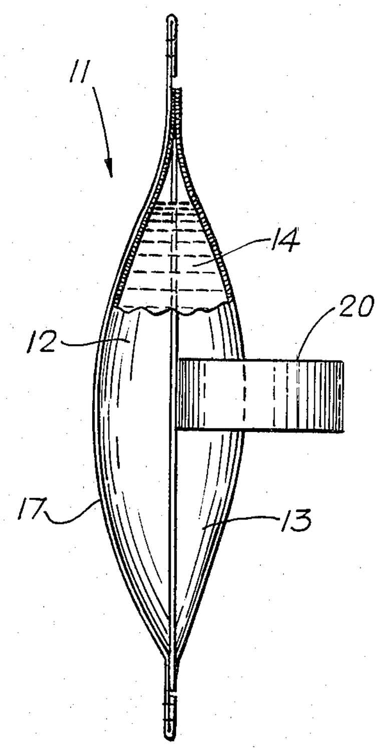
FIG. 2 is a side view, partially broken away, of the package.
Figure 3:
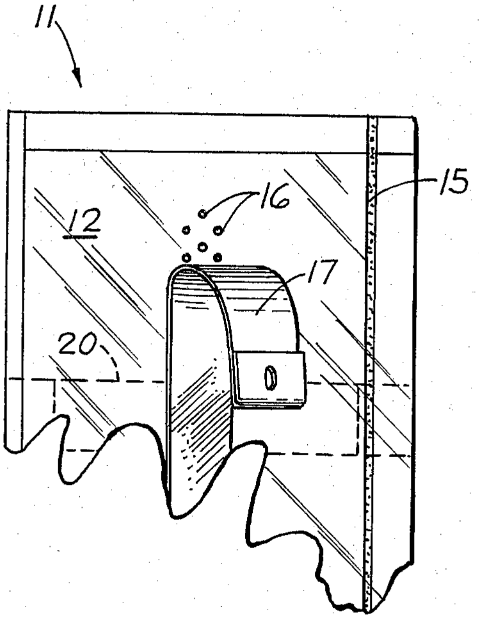
FIG. 3 is a fragmentary front view of the package showing the removable strip partially pulled away from the front wall of the container.
Figure 4:
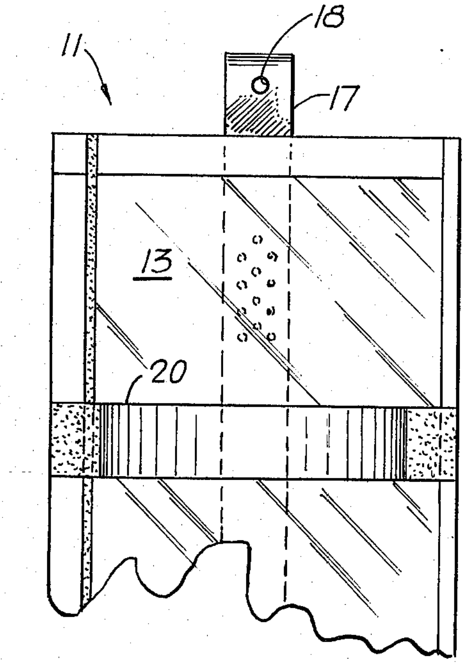
FIG. 4 is a fragmentary rear view of the package.

A safety eyewash package generally indicated at 11 includes front and rear flexible polyethylene sheets 12 and 13, respectively. Both have an illustrative wall thickness of about 0.5 mm. The sheets provide flexible front and rear walls of the container. The two sheets are rectangular and are about the same size. The top, bottom and end margins of the two sheets are sealed to each other. Before introduction of the liquid this sealing is provided at bottom and end margins. After introduction of an eyewash liquid 14 the top margin of the two sheets are sealed together. The seal can be as shown for the other margins or can be a seal 15 (FIG. 1) that is inwardly from the edge.

The sheet 12 has two sets of small holes 16 that are longitudinally spaced apart from each other, with the distance between two sets being approximately the average interpupillary distance.

The package 11 has a strip 17 of material that is impervious to the liquid and that is removably secured to the outside surface of front sheet 12. The strip 17 is positioned to overlie the two sets of holes 16 and extend beyond the two ends. Each of the end portions of strip 17 has a hole 18.

The safety eyewash package 11 is used to provide an emergency eyewash in the event some undesirable liquid gets into an eye. Because the package has this use in an emergency it can be referred to as an emergency eyewash package.

A strap 20 is connected at its end portions to the top and bottom margins of rear sheet 13. The strap 20 has sufficient length so that a hand can be placed between its intermediate portion and rear sheet 13 as shown in FIGS. 5–8.

To be available for emergency use, a number of packages 11 can be placed on a laboratory desk preferably with the rear sheet 13 and strap 20 facing upwardly. Also, preferably they would be stacked. In such use, of course, it would be unnecessary for strip 17 to have either of the two holes 18. When such packages 11 are stacked it is necessary for the person who has something in one or both of his eyes to place his hand between strap 20 and sheet 13 and then find and grasp strap 17.

To reduce the time of removal of strip 17 that is necessary before the application of the eyewash liquid package 11, strip 17 has hole 18 at one of its ends. This permits the mounting of a number of packages 11 on a hanger 21 mounted on a wall 22 on that hanger 21 is conveniently located above the laboratory desk. As seen in FIG. 5 hanger 21 has its distal or free end upwardly turned. The packages 11 are mounted by using hole 18 in strip 17 to feed strips 17 onto hanger 21. In an emergency the person moves his hand forward to a position where he knows that he will feel strap 20 of the outermost package of a set of packages 11. Then he can place his hand between strap 20 and rear sheet 13, move that package 11 forwardly until it is prevented from further easy forward movement by the hooked end of hanger 21. At that time the movement of the hand is such that sheet 12 is separated from strip 17 as shown in FIG. 5. By arm movement, package 11 can be rapidly turned to the position shown in FIG. 6 and moved up to the face where it is pushed by the hand against the face for a rapid streaming of liquid 14 from package 11 to the eyes.

The strip 17 shown in the drawings has a hole at each of its end portions. Of course, only one hole is needed for the use shown in FIG. 5. Either hole 18 can be used for mounting on hanger 21 but the orientation of package 11 should be such that strap 20 faces towards the user.

As seen in FIG. 7 the interpupillary distance between the two sets of holes 16, i.e., the distance between the center of each set, is such that the streams are directed toward the eyes and are not substantially directed toward the nose where the liquid would not provide the effective application required.

If only one eye is to be given an eyewash, package 11 having the two sets of holes 16 can be turned 90 degrees from that shown in its use in FIGS. 7 and 8 and placed so that one set is in front of the one eye to be rinsed. The other set is above that location to provide liquid that would flow down from the forehead and then over the eye to be treated. As the volume of liquid 14 in the package decreases, it may be possible to reorient the package so that both sets of holes 16 will provide streams of liquid 14 directly to that eye.

The foregoing description has been presented solely for the purpose of illustration and not by way of limitation of the invention because the latter is limited only by the claims that follow.

I claim:

1. A container useful for a sealed emergency safety eyewash package in which liquid, that is essentially water, is in the container, said container having a volumetric capacity of about one pint and consisting essentially of:

a front wall and a flexible rear wall constituting at least a major portion of the walls of the container; and a removable aqueous-impervious strip of material overlying only and secured only on a central longitudinal band of the outer surface of said front wall, said front wall being flexible to conform, when said container is sealed with water in it and after said strip has been removed, generally to the contour of an upper part of the human face, that includes the nose and both eyes, said front wall having holes only underlying and covered only by said strip, said holes being present as two sets, each of said sets having dimensions corresponding generally to an area overlying a human eye and said sets being spaced from each other a distance such that the distance between the center of each set is about the interpupillary distance for a human, said container when sealed and containing water and with said strip removed, being: impervious to water except at said holes; and constructed to permit movement of said rear wall toward said front wall restrained against further forward movement by the upper part of the human face, said holes in said two sets of holes in said front wall have dimensions that, for the sealed emergency eyewash package with said strip removed, are:

sufficiently small to preclude any substantial passage of water through said holes in said front wall; and sufficiently large to provide rapid streams of water flow from said holes during the period of time that, while said holes are overlying the eyes and other portions of said front wall are being flexed by pressing said front wall against the upper part of the human face, said rear wall is moved toward said front wall, said container further including a strap mounted on said rear wall of said container with said strap having a length so that fingers of a hand can be placed between the rear wall and the intermediate portion of said strap for manual support of said container and movement of it toward the face of the individual using the eyewash package after removal of said strip, said strap extending in a direction transverse to the direction of said strip at a plane passing through said strip between and generally equidistant from said sets of holes.

2. The container of claim 1 wherein it is constructed essentially with two flexible sheets of plastic that are sealed to each other at their bottom and end margins with the top margins of the two sheets being unsealed until the liquid is added.

3. The container of claim 2 wherein said strip extends beyond one of said end margins of said sheets and said extension has a hole.

4. A sealed eyewash package including said container of claim 1 and with essentially water in said container that is sealed.

5. The package of claim 4 wherein it is constructed with two flexible sheets of plastic that are sealed to each other at their top, bottom and end margins.

6. The package of claim 5 wherein said holes of said two sets of holes have a diameter of about 0.8 mm. and each of said plastic sheets has a thickness of about 0.5 mm.

* * * * *